(12) United States Patent
Langford et al.

(10) Patent No.: US 10,551,639 B2
(45) Date of Patent: Feb. 4, 2020

(54) OPHTHALMIC LENS COMMUNICATION TO DEVICE

(71) Applicant: Johnson & Johnson Vision Care, Inc., Jacksonville, FL (US)

(72) Inventors: Donald Scott Langford, Melbourne Beach, FL (US); Adam Toner, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 30 days.

(21) Appl. No.: 15/981,204

(22) Filed: May 16, 2018

(65) Prior Publication Data

US 2019/0353932 A1    Nov. 21, 2019

(51) Int. Cl.
| | |
|---|---|
| *G02C 7/04* | (2006.01) |
| *G02C 11/00* | (2006.01) |
| *G01S 11/14* | (2006.01) |
| *A61F 2/16* | (2006.01) |

(52) U.S. Cl.
CPC ............... *G02C 11/10* (2013.01); *A61F 2/16* (2013.01); *G01S 11/14* (2013.01); *G02C 7/04* (2013.01)

(58) Field of Classification Search
CPC .................. G02C 11/10; G02C 7/04

USPC ............ 351/159.03, 159.39, 159.73, 159.02, 351/159.01
See application file for complete search history.

(56) References Cited

U.S. PATENT DOCUMENTS

2018/0203260 A1*  7/2018  Blum ....................... G02C 7/04

* cited by examiner

*Primary Examiner* — Hung X Dang

(57) ABSTRACT

A powered ophthalmic lens having an electronic system is described herein configured to communicate with an external device using an ultrasound module for creating a sound pressure wave(s) to be transmitted through a medium, e.g. air, to an external device. The ophthalmic lens includes at least one ultrasound module having at least one transducer such as a pair of transmit and receive transducers, a transceiver transducer or a plurality of transducers. The ultrasound module includes additional components for the creation and reception of the sound pressure wave(s). In an alternative embodiment, there is one ultrasound module with a multiplexer connected to a plurality of transducers. In at least one embodiment, the sound pressure wave(s) encodes a message from the external device to the contact lens. In at least one alternative embodiment, the sound pressure wave(s) encodes a message from the contact lens to the external device.

24 Claims, 11 Drawing Sheets

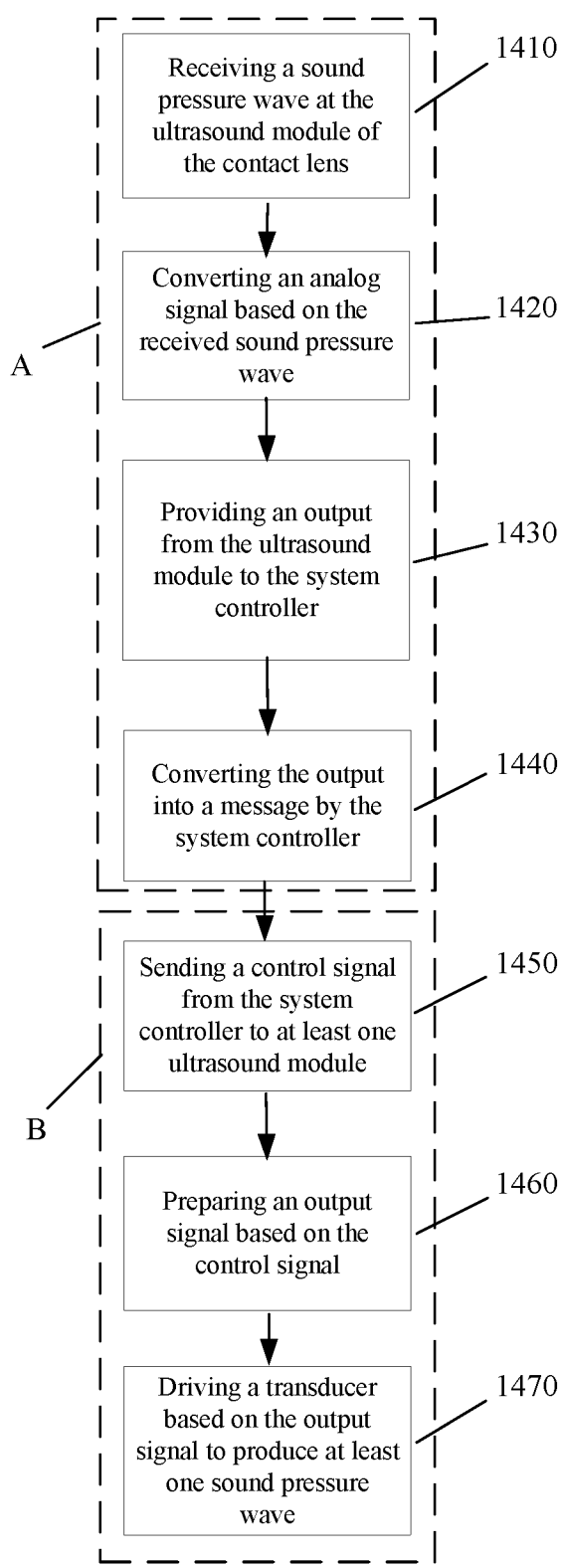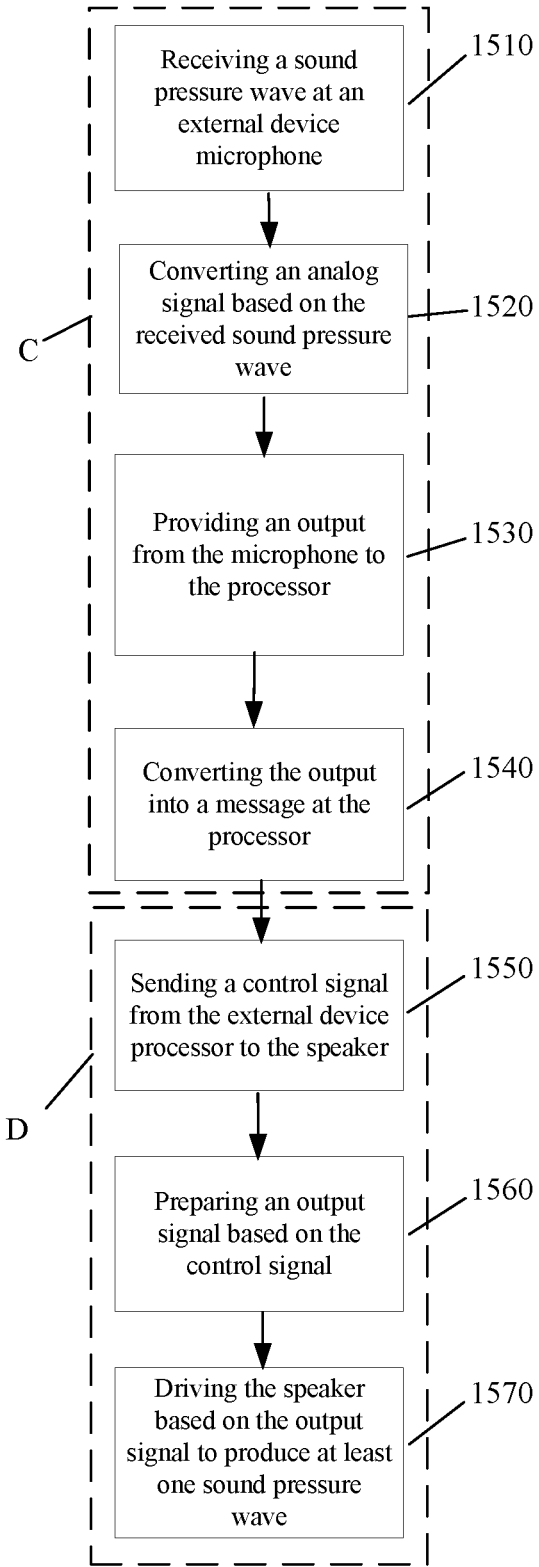
FIG. 14          FIG. 15

OPHTHALMIC LENS COMMUNICATION TO DEVICE

BACKGROUND OF THE INVENTION

1. Field of the Invention

The present invention relates to a powered or electronic ophthalmic lens, and more particularly, to a powered or electronic ophthalmic lens having an ultrasound module to provide a communication link to an external device.

2. Discussion of the Related Art

As electronic devices continue to be miniaturized, it is becoming increasingly more likely to create wearable or embeddable microelectronic devices for a variety of uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having an electronically adjustable focus to augment or enhance performance of the eye. In another example, either with or without adjustable focus, a wearable contact lens may incorporate electronic sensors to detect concentrations of particular chemicals in the pre-corneal (tear) film. The use of embedded electronics in a lens assembly introduces a potential requirement for communication with the electronics, for a method of powering and/or re-energizing the electronics, for interconnecting the electronics, for internal and external sensing and/or monitoring, and for control of the electronics and the overall function of the lens.

The human eye has the ability to discern millions of colors, adjust easily to shifting light conditions, and transmit signals or information to the brain at a rate exceeding that of a high-speed internet connection. Lenses, such as contact lenses and intraocular lenses, currently are utilized to correct vision defects such as myopia (nearsightedness), hyperopia (farsightedness), presbyopia and astigmatism. However, properly designed lenses incorporating additional components may be utilized to enhance vision as well as to correct vision defects.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered ophthalmic lenses may be designed to provide enhanced vision via zoom-in and zoom-out capabilities, or just simply modifying the refractive capabilities of the lenses. Electronic and/or powered contact lenses may also be designed to enhance color and resolution.

The proper combination of devices could yield potentially unlimited functionality; however, there are a number of difficulties associated with the incorporation of extra components on a piece of optical-grade polymer. In general, it is difficult to manufacture such components directly on the lens for a number of reasons, as well as mounting and interconnecting planar devices on a non-planar surface. It is also difficult to manufacture to scale. The components to be placed on or in the lens need to be miniaturized and integrated onto just 1.5 square centimeters of a transparent polymer while protecting the components from the liquid environment on the eye. It is also difficult to make a contact lens comfortable and safe for the wearer with the added thickness of additional components.

In addition, because of the complexity of the functionality associated with a powered lens and the high level of interaction between all of the components comprising a powered lens, there is a need to coordinate and control the overall operation of the electronics and optics comprising a powered ophthalmic lens. Accordingly, there is a need for a system to control the operation of all of the other components and provide communication between the contact lenses that is safe, low-cost, and reliable, has a low rate of power consumption and is scalable for incorporation into an ophthalmic lens. Accordingly, there exists a need for a means and method for communicating between ophthalmic lenses while they are being worn and/or with an external device.

There are several scenarios where there is a need for powered contact lenses to communicate during normal operation. Methods of detecting and changing lens state for presbyopia, commonly referred to as accommodation, may require the state of the left and right eye to be shared to determine if the lens focus should be changed. In each case, the independent state of each eye must be communicated so that the system controller can determine the required state of the variable lens actuator. There are other cases where it may enhance the user experience if the lens state (e.g., focus state) is changed in a coordinated fashion.

SUMMARY OF THE INVENTION

Lens-to-external device communication may take place wirelessly. There are at least three approaches to communicate lens-to-lens: photonic (light), radio frequency (RF) and ultrasound communication. Communication using light is difficult as the power consumption associated with generating photonic signals sufficiently powerful to overcome ambient interference may be prohibitive for the lens power source. RF signal generation may be possible but challenging. Higher RF frequency signals are required to operate with antennas that are sized to fit within a typical contact lens application. Generation of higher frequency signals typically require more power due to less efficient sources. RF energy is absorbed by human tissue thus reducing power at the receiver. Ultrasound communication is desirable as the sound spectrum is unregulated and there are few background ultrasound signals. The required ultrasound frequency is orders of magnitude lower than required RF frequency for a similar application. The power level required to generate ultrasound signals is therefore lower than RF signals for a similar application. Ultrasound energy has significantly less absorption in the human body. Due to the lower absorption, the allowed power levels for safe ultrasound energy operation in the body are orders of magnitude higher than RF energy limits.

In at least one embodiment, an ophthalmic lens system configured for ultrasound communication with an external device includes: at least one ophthalmic lens; at least one ultrasound module in the ophthalmic lens, at least one of the at least one ultrasound module includes at least one transducer front-facing and orientated such that when a sound pressure wave is produced, the sound pressure wave travels outwardly from the ophthalmic lens, a system controller in electrical communication with the at least one ultrasound module, the system controller configured to provide a control signal to the at least one ultrasound module where the control signal includes a message to be transmitted by the at least one ultrasound module, the system controller configured to receive an output from the at least one ultrasound module and to perform a function in response to a receive message embodied in the output, and a timing circuit in electrical communication with the system controller, the timing circuit configured to produce a timing signal when the system controller is activated. In a further embodiment to the previous embodiment, the at least one ultrasound module includes a plurality of ultrasound modules evenly distributed around a perimeter of the ophthalmic lens. In a further embodiment to the previous embodiment, the system controller is configured to activate the ultrasound module that produces the strongest output in response to a received sound pressure wave, and the system controller configured to deactivate the at least one other ultrasound module on the ophthalmic lens.

In a further embodiment to any of the embodiments in the previous paragraph, the at least one transducer includes a transmit transducer and a receive transducer, and each ultrasound module includes a processor in electrical communication with the system controller; a transmit path having an oscillator in electrical communication with the processor, a burst generator in electrical communication with the oscillator and the processor, a transmit driver in electrical communication with the burst generator configured to receive a burst signal from the burst generator, the transmit transducer in electrical communication with the transmit driver; and at least one receive path having the receive transducer, a receive amplifier in electrical communication with the receive transducer and configured to amplify an output of the receive transducer, and an analog signal processor in communication with the receive amplifier and the processor, and wherein the processor configured to control whether the transmit path and the at least one receive path are activated. In a further embodiment to the previous embodiment, each ultrasound module includes two receive paths, the two receive paths each having the receive transducer tuned to different frequencies from the other receive paths. In a further embodiment to any of the embodiments in the previous paragraph, the at least one ultrasound module includes three receive paths, the three receive paths each having the receive transducer tuned to different frequencies from the other receive paths. In a further embodiment to any of the embodiments in the previous paragraph, the at least one transducer is one transducer, and each ultrasound module includes a processor in electrical communication with the system controller; the transducer; a switch in electrical communication with the processor; a transmit path having an oscillator in electrical communication with the processor, a burst generator in electrical communication with the oscillator and the processor, a transmit driver in electrical communication with the burst generator configured to receive a burst signal from the burst generator, the transmit driver drives the transducer when connected through the switch; and at least one receive path having a receive amplifier in electrical communication with the transducer through the switch and configured to amplify an output of the transducer, and an analog signal processor in communication with the receive amplifier and the processor, and wherein the processor configured to control whether the transmit path and the at least one receive path are activated based on an operation mode of the ultrasound module between transmit and receive, and the processor configured to control the switch and the operation mode. In a further embodiment to any of the embodiments in the previous paragraph, each ophthalmic lens includes a power source in electrical communication with the system controller and the at least one ultrasound module; the at least one transducer includes a transmit transducer and a receive transducer; and each ultrasound module includes a processor in electrical communication with the system controller; a transmit path having an oscillator in electrical communication with the processor, a pulse generator in electrical communication with the oscillator and the processor, a charge pump in electrical communication with the power source, a transmit driver in electrical communication with the pulse generator and the charge pump, the transmit driver configured to receive a signal from the pulse generator, the transmit transducer in electrical communication with the transmit driver; and at least one receive path having the receive transducer, a receive amplifier in electrical communication with the receive transducer and configured to amplify an output of the receive transducer, and an envelope detector in electrical communication with the receive amplifier, an analog signal processor in communication with the envelope detector and the processor, and wherein the processor configured to control whether the transmit path and the at least one receive path are activated. In a further embodiment to any of the embodiments in the previous paragraph, each ophthalmic lens includes a power source in electrical communication with the system controller and the at least one ultrasound module; the at least one transducer includes a transmit transducer and a receive transducer, and each ultrasound module includes a processor in electrical communication with the system controller; a transmit path having an oscillator in electrical communication with the processor, an amplitude modulation modulator in electrical communication with the oscillator and the processor, a charge pump in electrical communication with the power source, a transmit driver in electrical communication with the amplitude modulation modulator and the charge pump, the transmit driver configured to receive a signal from the amplitude modulation modulator, the transmit transducer in electrical communication with the transmit driver; and at least one receive path having the receive transducer, a receive amplifier in electrical communication with the receive transducer and configured to amplify an output of the receive transducer, and an envelope detector in electrical communication with the receive amplifier, an analog signal processor in communication with the envelope detector and the processor, and wherein the processor configured to control whether the transmit path and the at least one receive path are activated.

In a further embodiment to any of the previous embodiments, at least one ultrasound module includes at least one transducer angled relative to an imaginary plane taken at a bottom edge of the ophthalmic lens on which the at least one transducer is located. In a further embodiment to any of the previous embodiments, the system further including a data storage unit in electrical communication with the system controller. In a further embodiment to the previous embodiment, the data storage unit includes at least one memory data register. In a further embodiment to any of the previous embodiments, the transducer in the at least one ultrasound module is configured to receive the sound pressure wave at a frequency of approximately 20 kHz.

In at least one embodiment, a method for facilitating communication between an ophthalmic lens when being used by a person where the ophthalmic lens includes at least one ultrasound module in electrical communication with a system controller, the ultrasound module having a forward facing transmit transducer, and an external device having at least a processor, a speaker and a microphone, the method including: receiving a sound pressure wave propagated by an external device at the ultrasound module; converting with the ultrasound module the sound pressure wave to an electrical signal; providing an output to the system controller from the ultrasound module; converting with the system controller the output into the message from the processor on the external device; sending a control signal from the system controller to the ultrasound module where the control signal embodies a transmission message intended for the external device; preparing an output signal for the transmit message by the ultrasound module; and driving the ultrasound module based on the output signal to produce at least one sound pressure wave.

In a further embodiment to the previous method embodiment, the method further including: receiving a sound pressure wave from an ophthalmic lens at the microphone on the external device; converting the received sound pressure wave to an electrical signal; providing an output to a processor; converting with the processor the received output to the message from the ophthalmic lens; sending a control signal with the processor embodying a message intended for the ophthalmic lens; driving the speaker based on the control signal to produce at least one sound pressure wave; receiving a sound pressure wave propagated by an external device at the ultrasound module; converting with the ultrasound module the sound pressure wave to an electrical signal; providing an output to the system controller from the ultrasound module; and converting with the system controller the output into the message from the processor on the external device. In a further embodiment to the previous embodiment, the sound pressure waves produced by the ophthalmic lens and external device are at different frequencies. In a further embodiment to the previous embodiment, the transducer in the at least one ultrasound module is tuned to the frequency of the output transducer of the external device and a second receive transducer in the at least one ultrasound module is tuned to the frequency of the ophthalmic lens.

In a further embodiment to the previous method embodiments, the ophthalmic lens includes a plurality of ultrasound modules evenly distributed around the periphery of the ophthalmic lens; and the method further including: selecting by the at least one system controller the ultrasound module that produces a strongest output in response to the received sound pressure wave propagated by the external device, and deactivating by the at least one system controller the non-selected ultrasound modules. In a further embodiment to the method embodiments in the previous paragraphs, the method further including deactivating the transmission components of the ultrasound module when not transmitting.

In a further embodiment to the previous method embodiments, the message sent by the system controller of the ophthalmic lens uses a predefined protocol and/or at least one of instructions for the external device to perform a predefined function and sensor readings from at least one sensor on the ophthalmic lens.

In a further embodiment to the previous method embodiments, the method further including: transmitting a start signal from the external device to each ophthalmic lens; receiving the start signal and tuning the frequency of the transmit transducer to a randomly selected frequency by the ultrasound module; propagating a sound pressure wave encoding a message identifying the selected frequency by the ultrasound module of each ophthalmic lens; decoding the messages from each ophthalmic lens and establishing communication protocol with each ophthalmic lens when the messages do not identify the same frequency.

In a further embodiment to any of the previous embodiments, the ophthalmic lens is a contact lens or an intraocular lens.

Further to the previous embodiments, the ophthalmic lens includes an intraocular lens and/or a contact lens.

Further to any of the embodiments above, a message sent by the system controller of the first ophthalmic lens uses a predefined protocol. Further to any of the embodiments above, the message sent by the system controller of the first ophthalmic lens includes instructions for the second ophthalmic lens to perform a predefined function. Further to any of the embodiments above, the message sent by the system controller of the first ophthalmic lens includes sensor readings from at least one sensor on the first ophthalmic lens.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 14 illustrates a communication method for a contact lens to an external device in accordance with at least one embodiment of the present invention.

FIG. 15 illustrates a communication method for an external device to a contact lens in accordance with at least one embodiment of the present invention.

DETAILED DESCRIPTION OF THE EMBODIMENTS

Figure 1:
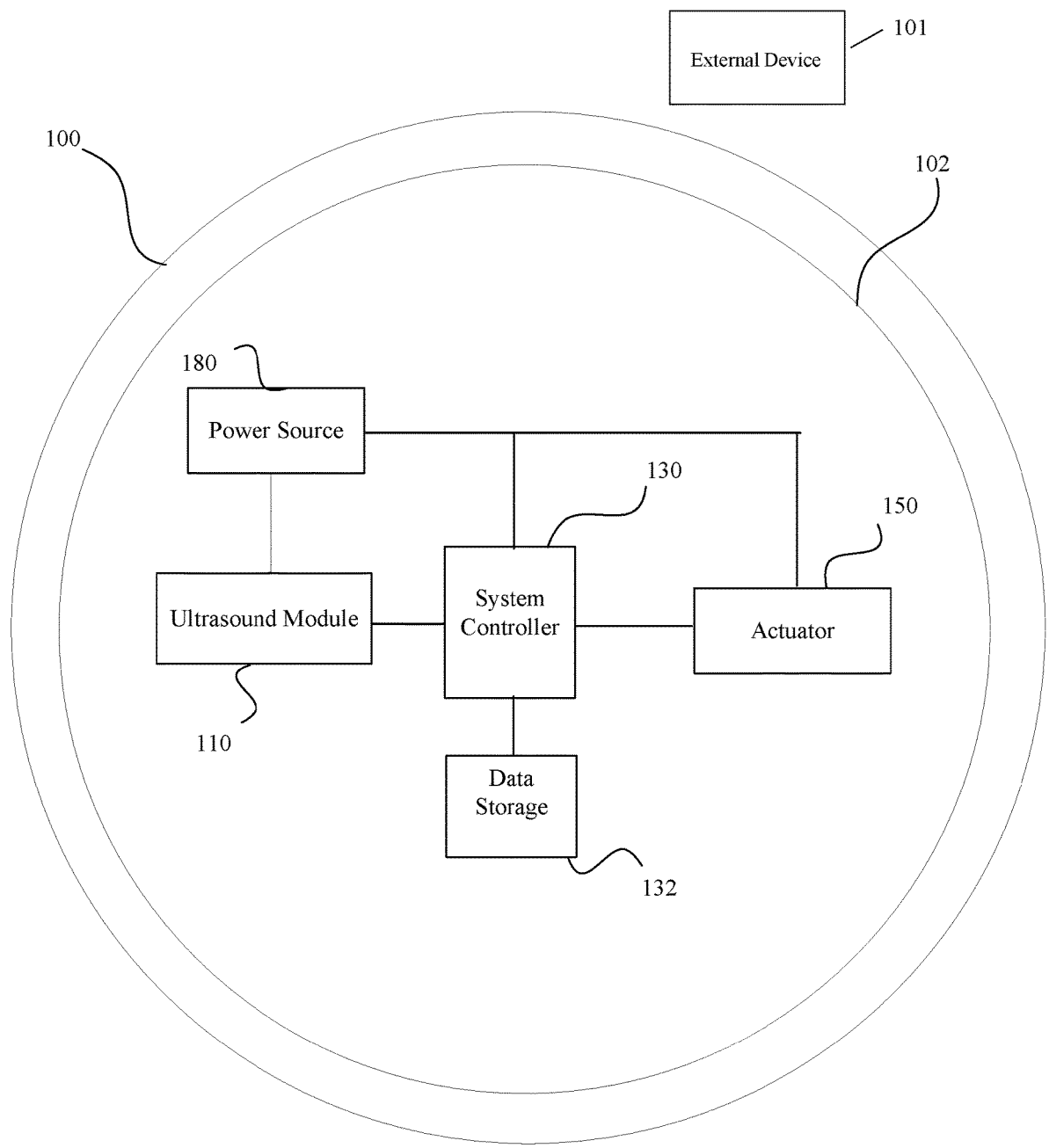
FIG. 1 illustrates a contact lens having at least one ultrasound module in accordance with at least one embodiment of the present invention.

Conventional contact lenses are polymeric structures with specific shapes to correct various vision problems as briefly set forth above. To achieve enhanced functionality, various circuits and components may be integrated into these polymeric structures. For example, control circuits, microprocessors, communication devices, power supplies, sensors, ultrasound modules, and miniature antennas may be integrated into contact lenses via custom-built optoelectronic components to not only correct vision, but to enhance vision as well as provide additional functionality as is explained herein. Electronic and/or powered contact lenses may be designed to provide enhanced vision via zoom-in and zoom-out capabilities, or just simply modifying the refractive capabilities of the lenses. Electronic and/or powered contact lenses may be designed to enhance color and resolution. In at least one embodiment, ultrasound modules built into the lenses are utilized to communicate with one or more external devices.

The powered or electronic contact lens in at least one embodiment includes the necessary elements to monitor the wearer with or without elements to correct and/or enhance the vision of the wearer with one or more of the above described vision defects or otherwise perform a useful ophthalmic function. The electronic contact lens may have a variable-focus optic lens, an assembled front optic embedded into a contact lens or just simply embedding electronics without a lens for any suitable functionality. The electronic lens of the present invention may be incorporated into any number of contact lenses as described above. In addition, intraocular lenses may also incorporate the various components and functionality described herein. However, for ease of explanation, the disclosure will focus on an electronic contact lens intended for single-use daily disposability.

The present invention may be employed in a powered ophthalmic lens or powered contact lens having an electronic system, which actuates a variable-focus optic or any other device or devices configured to implement any number of numerous functions that may be performed. An ophthalmic lens includes a contact lens and an intraocular lens. The electronic system includes one or more batteries or other power sources, power management circuitry, one or more sensors, clock generation circuitry, control algorithms and circuitry, and lens driver circuitry. The complexity of these components may vary depending on the required or desired functionality of the lens.

Control of an electronic or a powered ophthalmic lens may be accomplished through a manually operated external device that communicates with the lens through ultrasonic communication, such as a hand-held remote unit, a phone, a storage container, spectacles, or a cleaning box. For example, an external device may wirelessly communicate using ultrasound with the powered lens based upon manual input from the wearer through an external device. Alternatively, control of the powered ophthalmic lens may be accomplished via feedback or control signals directly from the wearer. In at least one embodiment, the ultrasound module includes a transmit ultrasound transducer and at least one receive ultrasound transducer, a combination transmit/receive ultrasound transducer, or a combination passive transmit/receive backscatter ultrasound transducer. Based upon the communication message, the powered ophthalmic lens may change operation state such as change focus of the contact lens.

Because of the complexity of the functionality associated with a powered lens and the high level of interaction between all of the components comprising a powered lens, there is a need to coordinate and control the overall operation of the electronics and optics comprising a powered ophthalmic lens. Accordingly, there is a need for a system to control the operation of all of the other components and provide communication with an external device and possibly between the contact lenses that is low-cost and reliable, has a low rate of power consumption, and is scalable for incorporation into an ophthalmic lens.

FIGS. 1-9 and 13 illustrate different embodiments according to the invention that include a system controller 130 connected to a timing circuit 140 and an ultrasound module (collectively referred to as 110) that are on a contact lens 100. The ultrasound module 110 may take a variety of forms including distinct transmit and receive transducers or a shared transmit/receive transducer. Depending on a particular implementation, there may be multiple ultrasound modules 110 present on the contact lens 100 to facilitate particular functionality for the ophthalmic lens or alternatively multiple transducers connected to one or more ultrasound modules 110. Many of the figures include an actuator 150 as part of the system with the actuator 150 being representative of, for example, lens accommodation components, data collection components, data monitoring components, and/or functional components such as an alarm. The external device 101 is illustrated proximate to the contact lens 100.

The system controller 130 in at least one embodiment uses at least one predetermined threshold or template for interpreting the output of the ultrasound module 110. In another embodiment, the system controller 130 makes use of at least one template (or pattern) to which a series of outputs of the ultrasound module 110 are compared against to determine whether the template has been satisfied, for example, based on a match to the pattern and/or a threshold being met, exceeded or less than resulting in the template being satisfied. In at least one embodiment, the template includes only at least one threshold. In an alternative embodiment, both thresholds and patterns are used by the system controller 130 to interpret a received series of sound pressure waves. In at least one embodiment as illustrated in FIG. 1, the system controller 130 is in electrical communication with a data storage 132 that stores the threshold(s) and/or template(s). In at least one embodiment, a plurality of templates includes any combination of patterns and thresholds. Examples of data storage 132 include memory such as persistent or non-volatile memory, volatile memory, and buffer memory, a register(s), a cache(s), programmable read-only memory (PROM), programmable erasable memory, magneto resistive random access memory (RAM), ferro-electric RAM, flash memory, and polymer thin film ferroelectric memory. In an alternative embodiment, the output(s) of the ultrasound module 110 to the system controller 130 is converted by the system controller 130 into data for control of the actuator 150. In an alternative embodiment, the system controller 130 interprets the output of the ultrasound module 110 using a predefined protocol.

FIG. 1 illustrates a system on a contact lens 100 having an electro-active region 102 with an ultrasound module 110, a system controller 130, an actuator 150, and a power source 180. In at least one further embodiment, the electro-active region 102 includes an electronics ring around the contact lens 100 on which the electronics are located. The ultrasound module 110 in at least one embodiment has two-way communication with the system controller 130. The actuator 150 receives an output from the system controller 130. In at least one alternative embodiment, the actuator 150 is omitted from one or more of the illustrated embodiments in this disclosure.

The actuator 150 may include any suitable device for implementing a specific function based upon a received command signal from the system controller 130. For example, if a set of data samples matches a template, the system controller 130 may enable the actuator 150 to change focus of the contact lens, provide an alert to the wearer, for example, using a light (or light array) to pulse a light or cause a physical wave to pulsate into the wearer's retina (or alternatively across the lens), or to log data regarding the state of the wearer. Further examples of the actuator 150 acting as an alert mechanism include an electrical device; a mechanical device including, for example, piezoelectric devices, transducers, vibrational devices, chemical release devices with examples including the release of chemicals to cause an itching, irritation or burning sensation, and acoustic devices; a transducer providing optic zone modification of an optic zone of the contact lens such as modifying the focus and/or percentage of light transmission through the lens; a magnetic device; an electromagnetic device; a thermal device; an optical coloration mechanism with or without liquid crystal, prisms, fiber optics, and/or light tubes to, for example, provide an optic modification and/or direct light towards the retina; an electrical device such as an electrical stimulator to provide a mild retinal stimulation or to stimulate at least one of a corneal surface and one or more sensory nerves of the cornea; or any combination thereof. In an alternative embodiment, the actuator 150 sends an alert to an external device using, for example, the ultrasound module 110. The actuator 150 receives a signal from the system controller 130 in addition to power from the power source 180 and produces some action based on the signal from the system controller 130. For example, if the output signal from the system controller 130 occurs during one operation state, then the actuator 150 may alert the wearer that a medical condition has arisen or the contact lens is ending/nearing its useful life and/defective. In an alternative embodiment, the actuator 150 delivers a pharmaceutical product to the wearer in response to an instruction from the system controller 130. In an alternative embodiment, the output signal from the system controller 130 during another operation state, may cause the actuator 150 to record the information in memory for later retrieval. In a still further alternative embodiment, the signal will cause the actuator 150 to alarm and store information. In an alternative embodiment, the system controller 130 stores the data in the memory (e.g., data storage 132 in other embodiments) associated with the system controller 130 and does not use the actuator 150 for data storage and in at least one embodiment, the actuator 150 is omitted. As set forth above, the powered lens of the present invention may provide various functionality; accordingly, one or more actuators may be variously configured to implement the functionality.

FIG. 1 also illustrates a power source 180, which supplies power for numerous components in the system. The power may be supplied from a battery, energy harvester, or other suitable means as is known to one of ordinary skill in the art. Essentially, any type of power source 180 may be utilized to provide reliable power for all other components of the system. In an alternative embodiment, communication functionality is provided by an energy harvester that acts as the receiver for the time signal, for example, in an alternative embodiment, the energy harvester is a photovoltaic cell (in at least a contact lens embodiment), a photodiode (in at least a contact lens embodiment), or a radio frequency (RF) receiver, which receives both power and a time-base signal (or indication). In a further alternative embodiment, the energy harvester is an inductive charger, in which power is transferred in addition to data such as RFID. In one or more of these alternative embodiments, the time signal could be inherent in the harvested energy, for example N*60 Hz in inductive charging, lighting, or sound including ultrasound.

Figure 2:
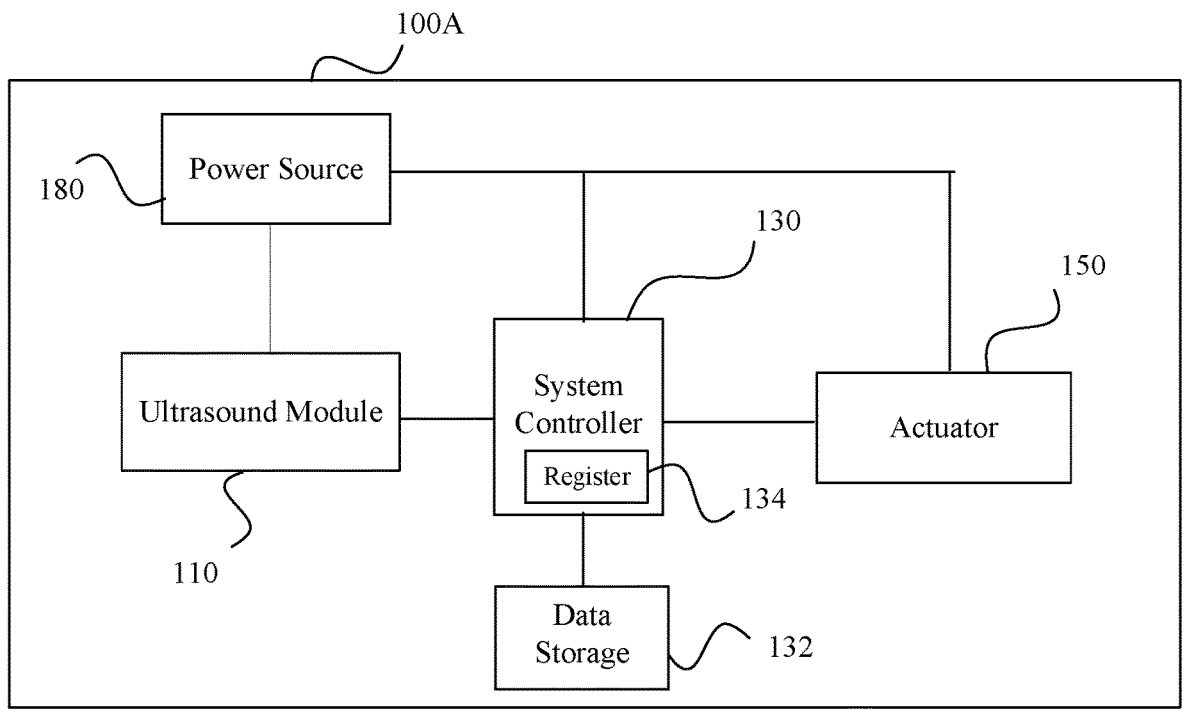
FIG. 2 illustrates a contact lens having at least one ultrasound module and a system controller having a register in accordance with at least one embodiment of the present invention.

In at least one embodiment as illustrated in FIG. 2, the contact lens 100A includes the system controller 130 having a register 134 for storing data samples from the ultrasound module 110. In a further embodiment, there is an individual register 134 for each ultrasound module 110 and/or a receiving transducer present on the contact lens 100A. The use of a register 134 in at least one embodiment allows for the comparison of data with prior data, a threshold, a preset value, a calibrated value, a target processing value, or a template with or without a mask. In an alternative embodiment, other data storage is used instead of a register(s). In an alternative embodiment, the register 134 is part of the data storage 132.

Based on this disclosure, it should be appreciated that in addition to the presence of the ultrasound module 110 on the contact lens 100 that additional sensors may be included as part of the contact lens to monitor characteristics of the eye and/or the lens. In at least one embodiment, at least a portion of the actuator 150 is consolidated with the system controller 130.

Figure 3:
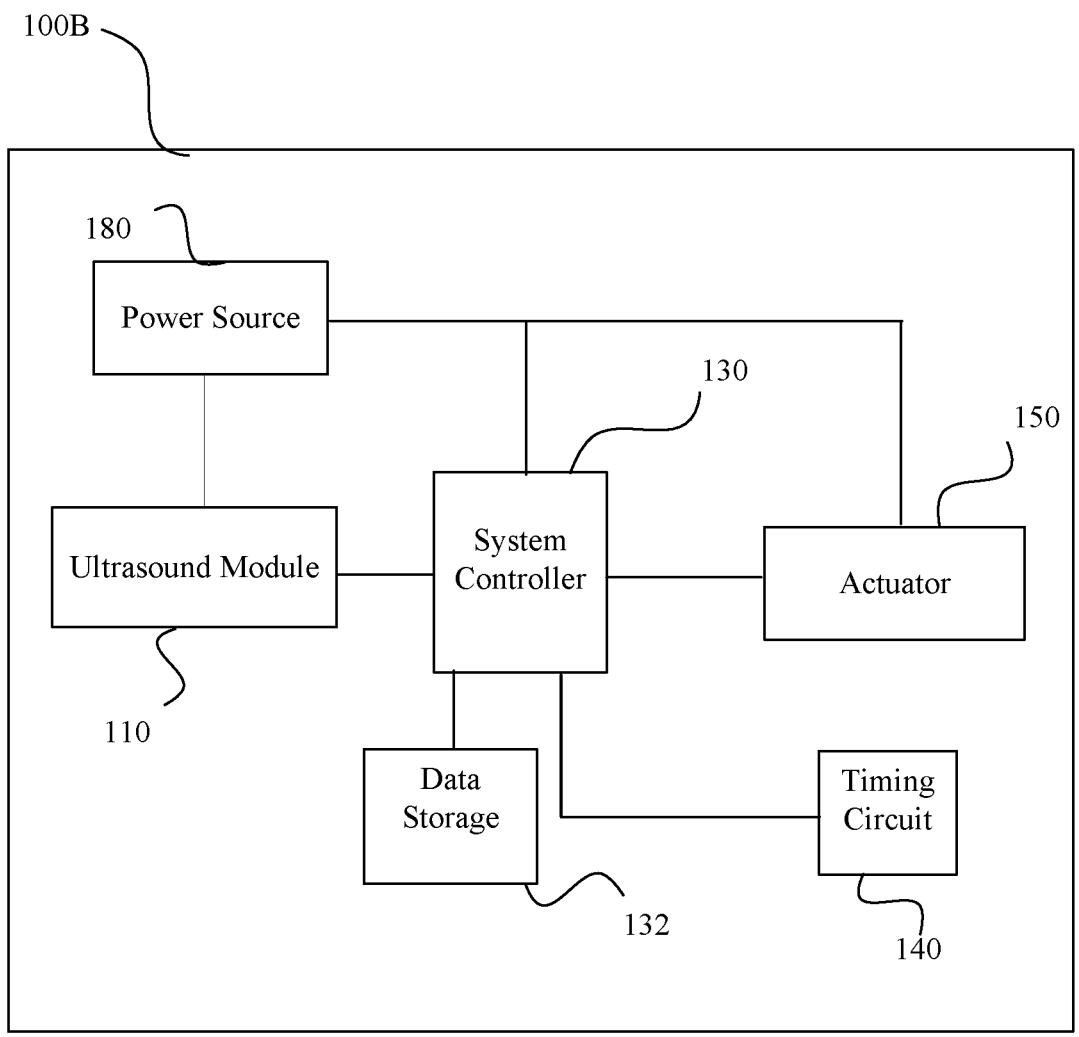
FIG. 3 illustrates a contact lens having at least one ultrasound module and a timing circuit in accordance with at least one embodiment of the present invention.

FIG. 3 illustrates another contact lens 100B that adds a timing circuit 140 to the system illustrated in FIG. 1. In an alternative embodiment, the timing circuit 140 may also be added to the embodiment illustrated in FIG. 2. The timing circuit 140 provides a clock function for operation of the contact lens. As illustrated, the timing circuit 140 is connected to the system controller 130. In at least one embodiment, the timing circuit 140 drives the system controller 130 to send a signal to the ultrasound module 110 to perform a function based on a sampling time interval, which in at least one embodiment is variable based on the output from the ultrasound module 110 to the system controller 130. In an alternative embodiment, the timing circuit 140 is part of the system controller 130.

FIGS. 4-9 and 13 illustrate different ultrasound modules that illustrate different transmit paths and receive paths examples of paths that facilitate transmitting and receiving sound pressure waves from one or more transducers 116, 121 that start or end with a processor 111 and/or the system controller 130 depending on the example embodiment.

Figure 4:
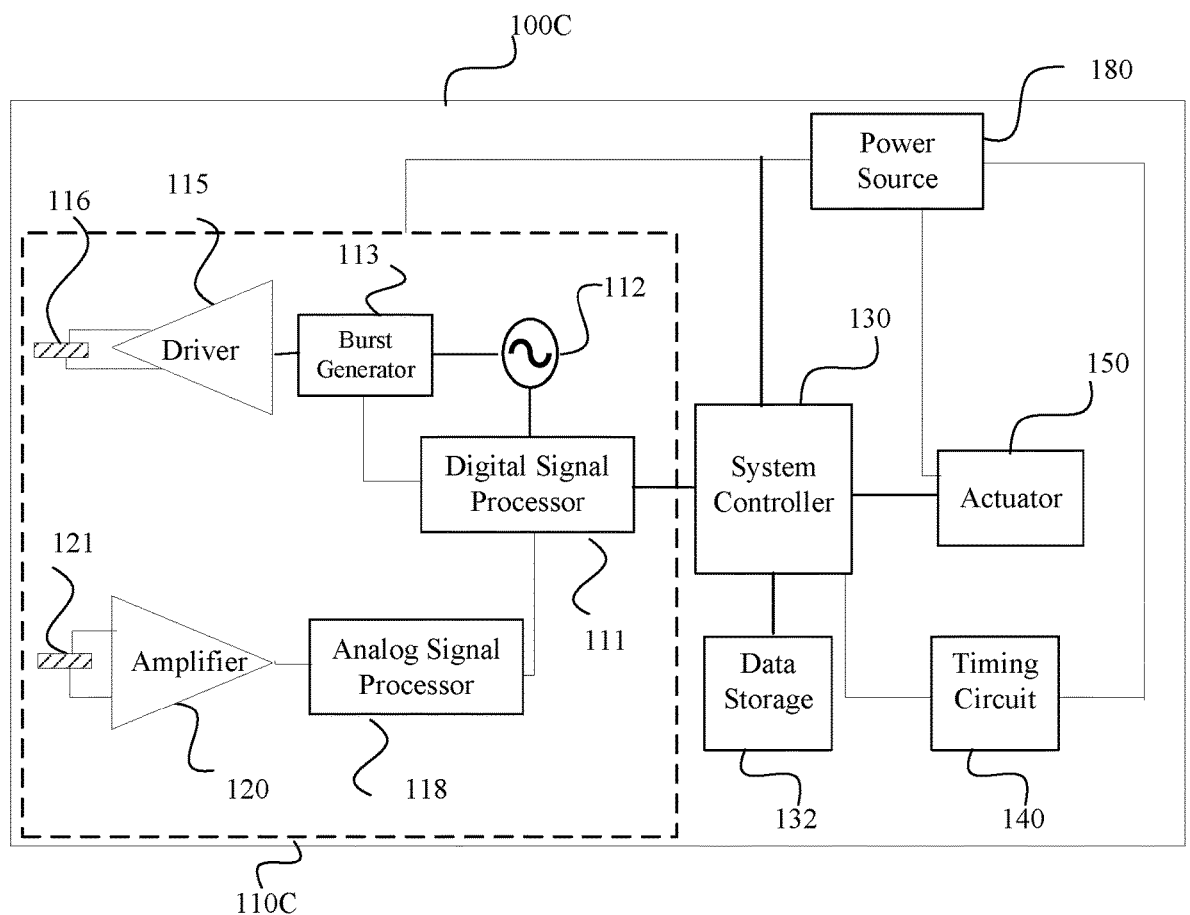
FIG. 4 illustrates an ultrasound module in accordance with at least one embodiment of the present invention.

FIG. 4 illustrates a contact lens 100C that includes an ultrasound module 110C having distinct transmit and receive sides. The illustrated ultrasound module 110C includes a digital signal processor 111, an oscillator 112, a burst generator 113, a transmit driver 115, a transmit ultrasound transducer 116, an analog signal processor 118, a receive amplifier 120, and a receive ultrasound transducer 121. In at least one embodiment, the burst generator 113 produces a series of 1's and 0's to facilitate communication with another lens and/or an external device. In at least one embodiment, the burst generator 113 incorporates a unique identifier for the contact lens based on the amplitude, the frequency, the length, and/or the code modulation of the signal. In a further embodiment, the unique identifier is provided by the system controller 130, the digital signal processor 111, the oscillator 112, and/or the burst generator 113. A similar use of a unique identifier may be used with the other embodiments in this disclosure. In at least one alternative embodiment for the ultrasound module 110C, the digital signal processor 111 is combined with the system controller 130. In another alternative embodiment, the analog signal processor 118 is combined with the digital signal processor 111 and/or replaced with an analog-to-digital converter as illustrated in a later figure. These two alternative embodiments may be combined to provide a further alternative embodiment.

The digital signal processor 111 receives a control signal from the system controller 130. In at least one embodiment, the digital signal processor 111 includes a resettable counter and a time-to-digital converter and transmit/receive sequencing controls. The oscillator 112 in at least one embodiment is a switched oscillator. In at least one embodiment, the frequency of the oscillator 112 is programmable through a preset oscillator value, the system controller 130 or external interface (e.g., an interface with an external device 101). The frequency may be tuned using a reference oscillator and an external interface. In at least one further embodiment, the frequency is set or tuned to a value that minimizes transmit and receive electrical power and allows the transmit ultrasound transducer 116 to produce a pressure sound wave that will have maximum amplitude at the receiver input. In a more particular embodiment, the oscillator 112 is a programmable frequency oscillator such as a current starved ring oscillator where the current and the capacitance control the oscillation frequency where the frequency may be altered by changing the current supplied to the oscillator. In at least one embodiment, the wavelength of the sound pressure wave is tuned based on the dimensions of the transducer used. In a further embodiment, the oscillator 112 varies over time for optimal transmission characteristics. In a still further embodiment, the frequency is calibrated using a reference frequency provided through an external interface and an automatic frequency control (AFC) circuit. The frequency is preset with the AFC tuning it. The frequency can be directly set through the serial interface, which is accessed through the external communications link.

The output voltage of the burst generator 113 may be level shifted to the appropriate value for the transmit driver 115 and the transmit ultrasound transducer 116. An example of the transmit ultrasound transducer 116 is a piezoelectric device which converts applied burst voltage to a sound pressure wave. In at least one embodiment, the sound pressure wave includes a burst or multiple sound pressure waves. In a further embodiment, the transmit ultrasound transducer 116 is made of any piezoelectric material that is compatible with the power source and the physical properties of the contact lens. The sound pressure wave produced by the transmit ultrasound transducer 116 propagates from the contact lens 100C into the field of view.

The receive amplifier 120 and the analog signal processor 118 in at least one embodiment are turned on with the oscillator 112 or turned on after a predetermined delay after the oscillator 112 is started. When there is a predetermined delay, power for contact lens operation may be lowered during the period of delay. In an embodiment where the receive amplifier 120 and the analog signal processor 118 are started with the oscillator 112, the receive amplifier 120 will receive an output from the receive ultrasound transducer 121 proximate to when the sound pressure wave is output by the transmit ultrasound transducer 116. This output from the receive ultrasound transducer 121, if desired, may be used to reset the counter in the digital signal processor 111. In a further embodiment, the detection of the transmit sound pressure wave may be used as an indicator that a true transmit signal has been generated.

A sound pressure wave received by the receive ultrasound transducer 121 will produce a voltage signal with frequency and burst length properties related to the transmitted sound pressure wave. The voltage signal is amplified by the receive amplifier 120 before being sent to the analog signal processor 118, which in an alternative embodiment to embodiments having the receive amplifier 120 and the signal processor 118 are combined into a signal processor. The analog signal processor 118 may include frequency selective filtering, envelope detection, integration, level comparison and/or analog-to-digital conversion. Based on this disclosure, it should be appreciated that these functions may be separated into individual blocks with some examples being illustrated in later figures. The analog signal processor 118 produces a received signal that represents the received sound pressure wave at the receive ultrasound transducer 121, which in implementation will have a slight delay. The received signal is passed from the analog signal processor 118 to the digital signal processor 111. When transmission time is used, the digital signal processor 111 will stop the counter that is counting pulses from the oscillator 112 when the received signal is received. In such an embodiment, the measured time can be compared to a predetermined value to determine whether a change in focus should occur. In other embodiments, the digital signal processor 111 interprets the received signal for a message from, for example, the external device or even another contact lens. The resulting output from the digital signal processor 111 is provided to the system controller 130.

Figure 5:
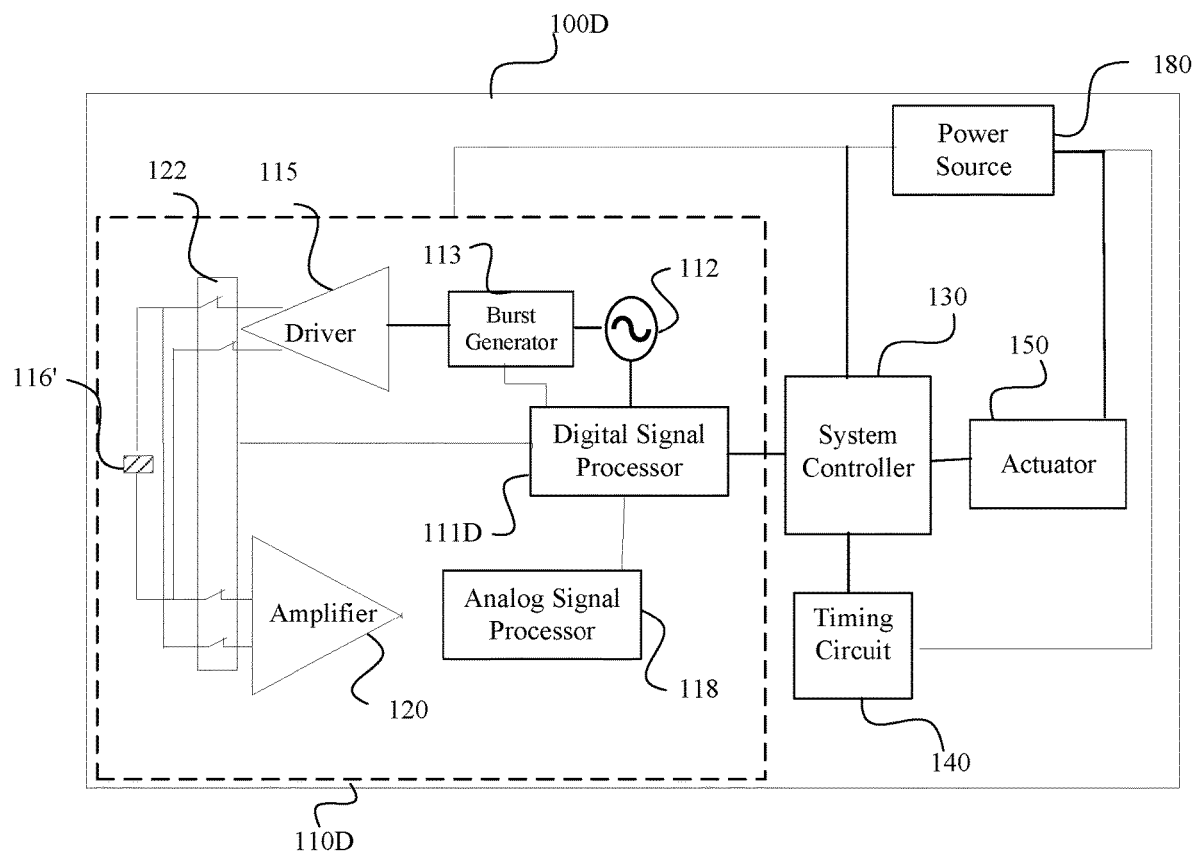
FIG. 5 illustrates an ultrasound module with one transducer and a multiplexer in accordance with at least one embodiment of the present invention.

FIG. 5 illustrates a contact lens 100D with an ultrasound module 110D. The illustrated ultrasound module 110D includes one ultrasound transducer 116' that is shared by the transmit and receive sides (or paths). The single ultrasound transducer 116' is multiplexed between transmit and receive operation through use of a switch 122. The digital signal processor 111D uses the output of the burst generator 113 to switch the transducer 116' to transmit mode by connecting the transmit driver 115 to the transducer 116'. When the burst is completed, then the digital signal processor 111D switches the switch 122 to the receive mode by connecting the receive amplifier 120 to the transducer 116'. One advantage to this configuration is that the transducer area is reduced from two transducers to one transducer, but a drawback to this configuration is that a received communication may be missed during a transmission or vice versa. As with the previous embodiment, a delay may be imposed after transmission before the receive amplifier 120 is powered. The remaining components of the illustrated embodiment remain the same from the prior embodiment.

Figure 6:
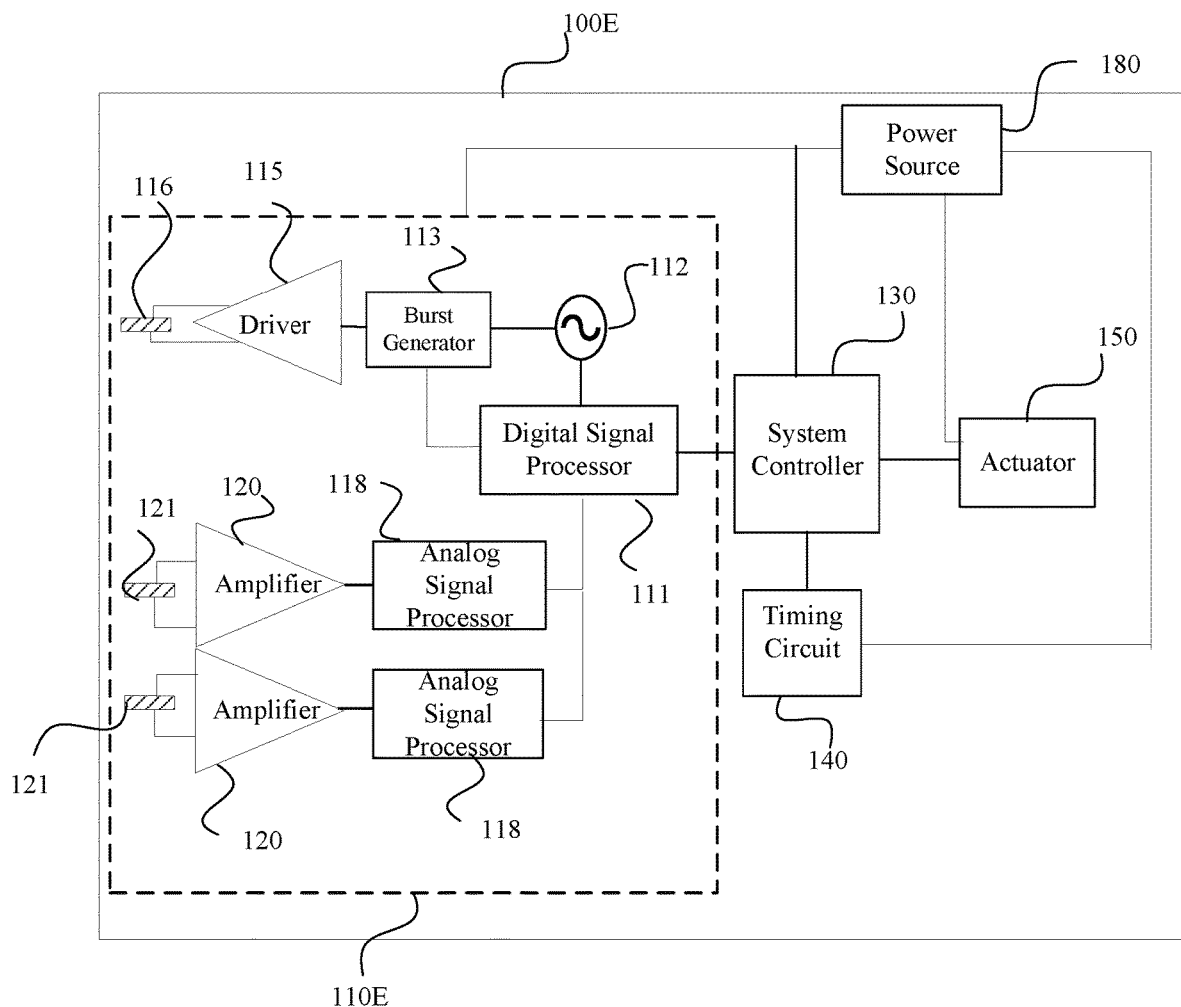
FIG. 6 illustrates an ultrasound module with two receive transducers in accordance with at least one embodiment of the present invention.

FIG. 6 illustrates a contact lens 100E where the receive side of the ultrasound module 110E includes two receive paths, which may be implemented in other embodiments. One advantage to this configuration is that the transducers could be configured for different sound frequencies to match the frequency of the transmit path of the contact lens 100E and the second receive path to match the transmission frequency of the external device. A similar approach may be adopted in the other embodiments where the receive transducer matches the transmission frequency of the external device. Each of the receive paths include a receive ultrasound transducer 121 electrically connected to a receive amplifier 120, which is electrically connected to an analog signal processor 118. The analog signal processors 118 are electrically connected to the digital signal processor 111. In a further embodiment, a third receive path could be added to have a transducer 121 tuned to the frequency of the other contact lens. The ultrasound module 110E also comprises the oscillator 112, the burst generator 113, and the transmit driver and the transmit ultrasound transduce 116.

Figure 7:
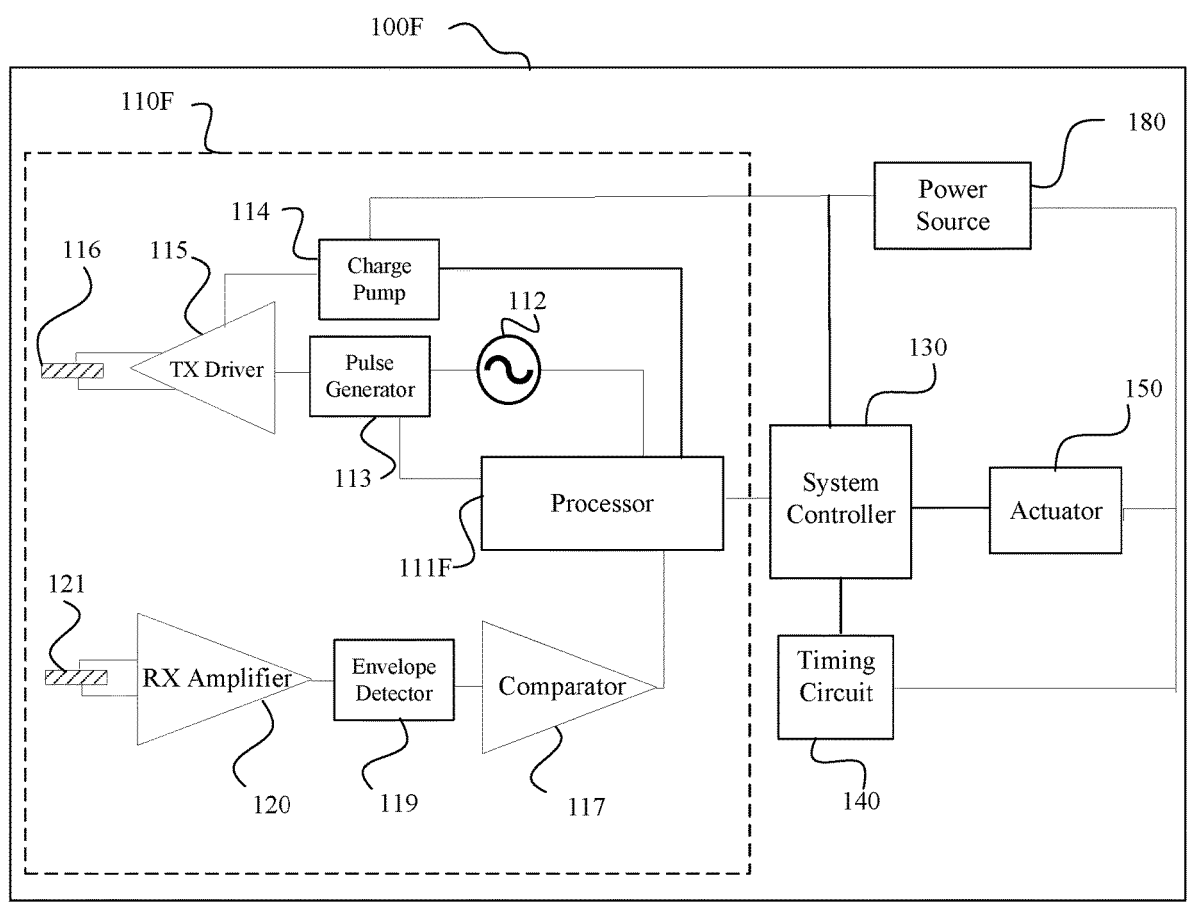
FIG. 7 illustrates an ultrasound module with two transducers, a charge pump and an envelope detector in accordance with at least one embodiment of the present invention.

FIG. 7 illustrates a contact lens 100F with an ultrasound module 110F. The illustrated ultrasound module 110F includes a processor 111F, the oscillator 112, the pulse generator 113, a charge pump 114, the transmit driver 115, the transmit ultrasound transducer 116, a comparator 117, an envelope detector 119, the receive amplifier 120, and the receive ultrasound transducer 121. The charge pump 114 is electrically connected to the power source 180 and to the transmit driver 115, which provides a voltage to the transmit ultrasound transducer 116 to create the sound pressure wave to be emitted by the transducer 116. In at least one embodiment, the transmit driver 115 includes an inverter or an H-bridge, and in further embodiments includes an output driver circuit. In at least one embodiment, the charge pump 114 increases the voltage through the relationship between charge and capacitance with voltage by increasing the charge on a capacitance component(s) (e.g., a capacitor). The voltage output from the charge pump 114, in at least one embodiment, is used as the supply voltage to the transmit driver 115. The transmit driver 115 switches between the output of the charge pump 114 and ground in an alternating fashion in response to the input from the pulse generator 113 to produce an alternating voltage. The alternating voltage is applied by the driver 115 to polarize the material of the transducer 116 in one direction and then the other direction to create a mechanical stress causing the material to be displaced in a specific direction (i.e. the direction the transducer is facing). The displacement of the transducer material coupled with the shape and the size of the transducer produce the sound pressure wave. Thus, the larger the applied voltage is to the transducer, the larger the stress and thus the larger the displacement and associated sound pressure wave.

The charge pump 114 is also electrically connected to the processor 111F, which controls the operation of the charge pump 114 in at least one embodiment to minimize power consumption by the system by, for example, turning off the oscillator 112, the pulse generator 113, and/or the charge pump 114 at times when the ultrasound module 110F does not need to propagate a sound pressure wave. The envelope detector 119 turns the high-frequency output of the receive ultrasound transducer 121 into a new signal that provides an envelope signal representative of the original output signal to be provided to the comparator 117. This illustrated embodiment has the advantage of simplifying the analysis of the output of the receive ultrasound transducer 121 to determine if a particular threshold has been met for the contact lens 100F to perform a function. The comparator 117 provides an output to the processor 111F, which is in electrical communication with the system controller 130.

Figure 8:
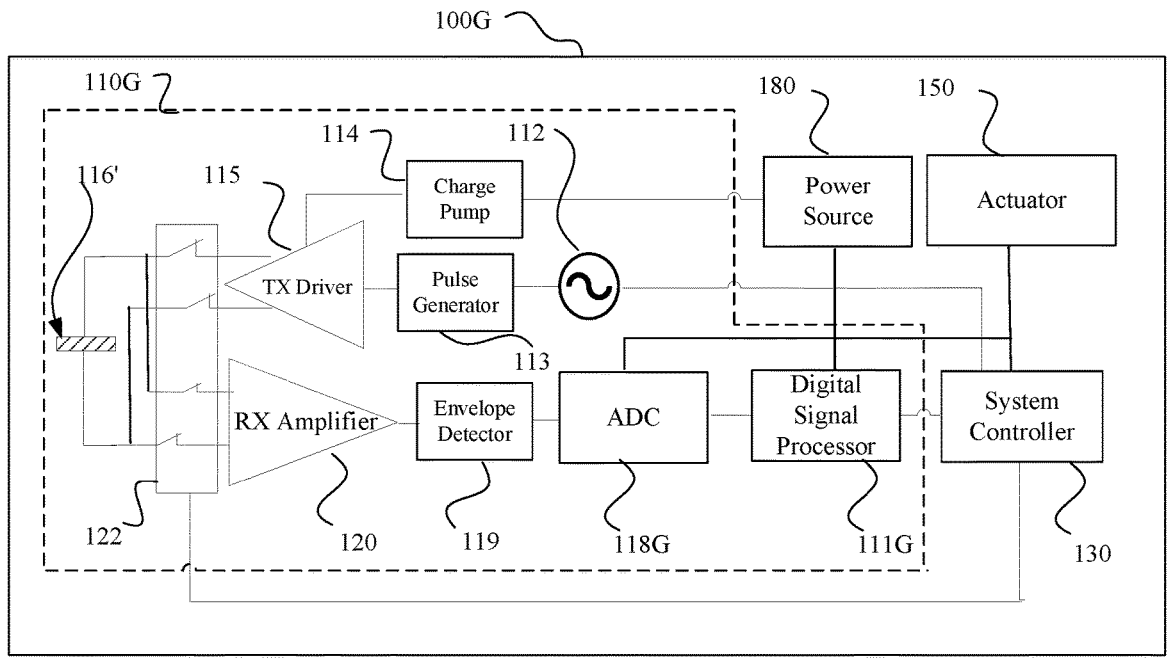
FIG. 8 illustrates an ultrasound module with one transducer and a multiplexer in accordance with at least one embodiment of the present invention.

FIG. 8 illustrates a contact lens 100G with an ultrasound module 110G. The illustrated ultrasound module 110G includes a digital signal processor 111G, the oscillator 112, the pulse generator 113, the charge pump 114, the transmit driver 115, the transmit/receive ultrasound transducer 116', an analog-to-digital converter (ADC) 118G, an envelope detector 119, the receive amplifier 120, and the switch 122. The ADC 118G converts the output from the envelope detector 119 into a digital signal for the digital signal processor 111G. The transmit/receive ultrasound transducer 116' and the switch 122 operate in the same manner as described above.

Figure 9:
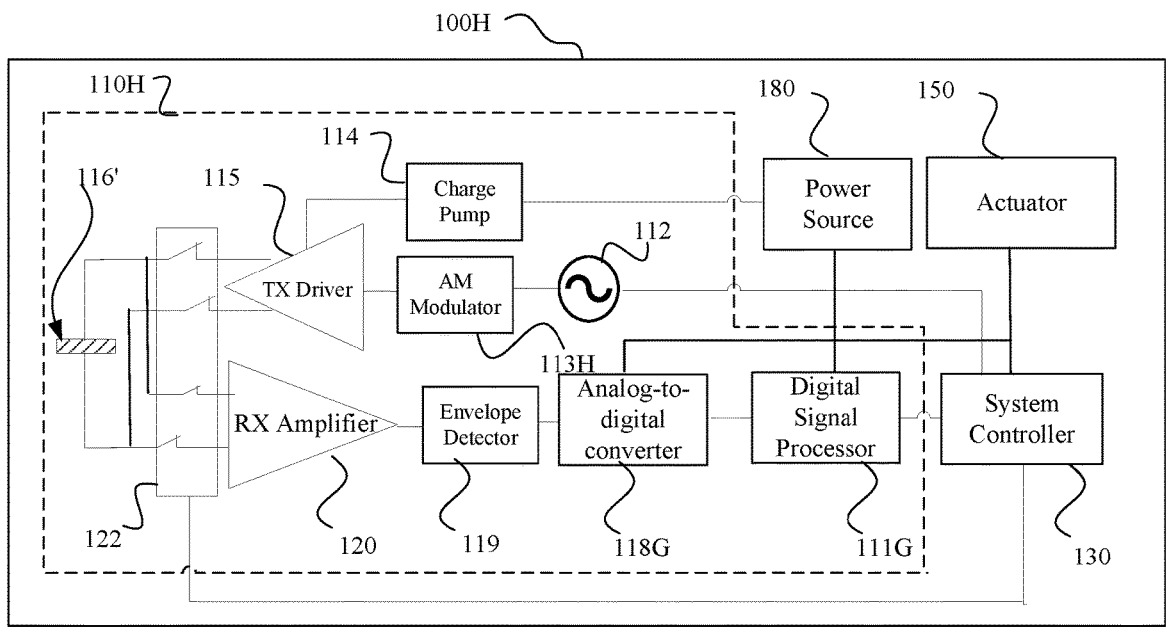
FIG. 9 illustrates an ultrasound module with one transducer and a multiplexer in accordance with at least one embodiment of the present invention.

FIG. 9 illustrates a contact lens 100H with an ultrasound module 110H. The illustrated ultrasound module 110H includes a digital signal processor 111G, the oscillator 112, an amplitude modulation (AM) modulator 113H, the charge pump 114, the transmit driver 115 such as a transmit amplifier, the transmit/receive ultrasound transducer 116', an analog-to-digital converter (ADC) 118G, an envelope detector 119, the receive amplifier 120, and the switch 122. In the illustrated embodiment, the charge pump 114, the AM modulator 113H and transmit driver 115 act as the level shifter and the burst generator. The AM modulator 113H in this embodiment is controlled by the digital signal processor 111G. The circuit works where the oscillator signal is provided to the AM modulator 113H, which in at least one embodiment is an AND gate, and the digital signal processor 111G provides a second clock at a frequency much lower than the oscillator frequency. The output of the circuit is then a sequence of pulses that occur during the positive cycle of the lower frequency. The transmit driver 115 has the appropriate gain to output the modulated signal at the charge pump voltage thus providing level shifting.

Based on the disclosure connected to FIGS. 7-9, one of ordinary skill in the art should appreciate that the different ultrasound module configurations and transducer/switch configurations may be interchanged and mixed together in different combinations.

Figure 10:
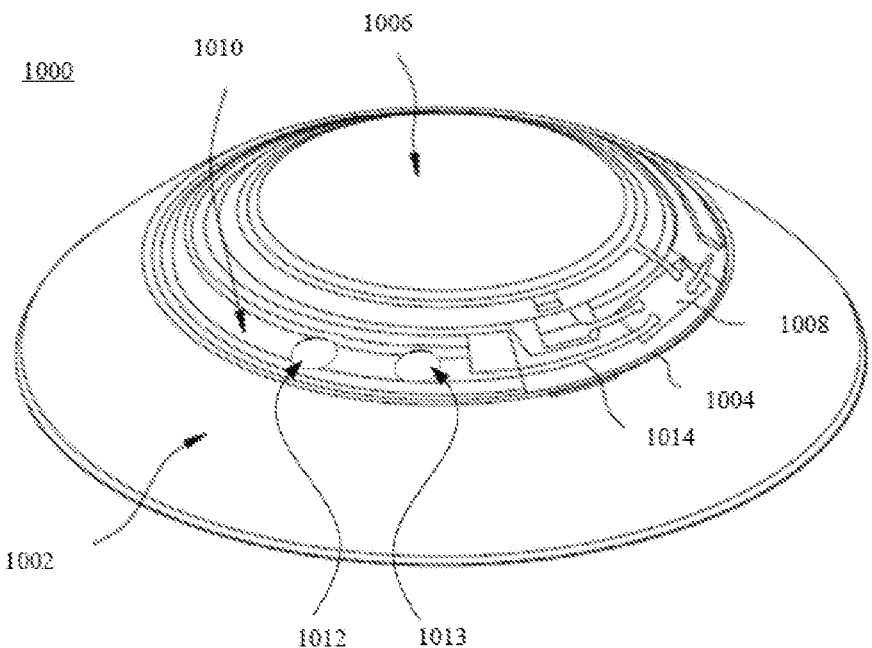
FIG. 10 illustrates a diagrammatic representation of an electronic insert, including a pair of transducers, for a powered contact lens in accordance with at least one embodiment of the present invention.

FIG. 10 illustrates a contact lens 1000 with an electronic insert 1004 having an ultrasound module. The contact lens 1000 includes a soft plastic portion 1002 which houses the electronic insert 1004, which in at least one embodiment is an electronics ring around a lens 1006. This electronic insert 1004 includes the lens 1006 which is activated by the electronics, for example, focusing near or far depending on activation (or accommodation level). In at least one embodiment, the electronic insert omits the adjustability of the lens 1006. Integrated circuit 1008 mounts onto the electronic insert 1004 and connects to batteries (or power source) 1010, lens 1006, and other components as necessary for the system.

In at least one embodiment, a transmit ultrasound transducer 1012 and a receive ultrasound transducer 1013 are present in the ultrasound module. In at least one embodiment, the integrated circuit 1008 includes a transmit ultrasound transducer 1012 and a receive ultrasound transducer 1013 with the associated signal path circuits. The transducers 1012, 1013 face outward through the lens insert and away from the eye (i.e., front-facing), and are thus able to send and receive sound pressure waves. In at least one embodiment, the transducers 1012, 1013 are fabricated separately from the other circuit components in the electronic insert 1004 including the integrated circuit 1008. In this embodiment, the transducers 1012, 1013 may also be implemented as separate devices mounted on the electronic insert 1004 and connected with wiring traces 1014. Alternatively, the transducers 1012, 1013 may be implemented as part of the integrated circuit 1008 (not shown). Based on this disclosure one of ordinary skill in the art should appreciate that transducers 1012, 1013 may be augmented by the other sensors.

Figure 11:
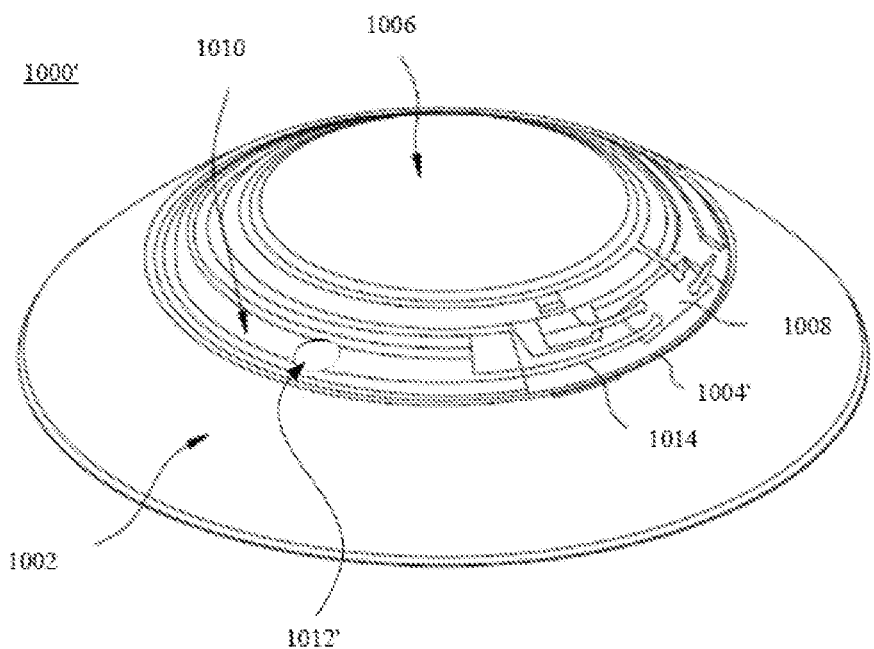
FIG. 11 illustrates a diagrammatic representation of an electronic insert, including a transducer, for a powered contact lens in accordance with at least one embodiment of the present invention.

FIG. 11 illustrates another contact lens 1000' with an electronic insert 1004' having an ultrasound module. The contact lens 1000' includes a soft plastic portion 1002 which houses the electronic insert 1004'. This electronic insert 1004' includes a lens 1006 which is activated by the electronics, for example, focusing near or far depending on activation (or accommodation level). In at least one embodiment, the electronic insert 1004' omits the adjustability of lens 1006. Integrated circuit 1008 mounts onto the electric insert 1004' and connects to batteries (or power source) 1010, lens 1006, and other components as necessary for the system. The ultrasound module includes a transmit/receive ultrasound transducer 1012' with the associated signal path circuits. The transducer 1012' faces outward through the lens insert and away from the eye and is thus able to send and receive sound pressure waves. As discussed above, the transducer 1012' may be fabricated separately from the other electronic components prior to mounting on the electronic insert 1004 or alternatively implemented on the integrated circuit 1008 (not shown). The transducer 1012' may also be implemented as a separate device mounted on the electronic insert 1004' and connected with wiring traces 1014. Based on this disclosure one of ordinary skill in the art should appreciate that transducer 1012' may be augmented by the other sensors.

In a further embodiment to the embodiments illustrated in FIGS. 10 and 11, the integrated circuit 1008, the power source 1010 and the transducers 1012, 1012', 1013 are present in an area of the contact lens contained in an overmold, which is a material (such as plastic or other protective material) encapsulating the electronic insert 1004. In at least one embodiment, the overmold encapsulates the ultrasound module(s).

In at least one embodiment, the electronics ring of FIGS. 10 and 11 includes an upper surface that is parallel with an imaginary plane on which the contact lens would rest. In at least one embodiment, the ultrasound transducers 1012, 1012', and 1013 are angled relative to the electronics ring and that plane. One example range of the relative angle is 0° to 90°, 0° to 90° including either or both endpoints, 15° to 30°, and 15° to 30° including either or both endpoints. The 0° would be flat to the electronics ring top surface while 90° would be at a right angle to the electronics ring top surface. A benefit to having the transducer angled relative to the electronics ring is to better aim the output sound pressure wave towards the nose of the wearer and thus cause scattering of the sound pressure wave to the other contact lens to facilitate direct contact lens to contact lens communication. In an alternative embodiment, the angled transducer would be for communicating with the other contact lens while a parallel transducer would be for communicating with the external device. In a further embodiment, these transducers could be in different ultrasound modules or in the same ultrasound module whether driven by the same transmit path or not.

Figure 12:
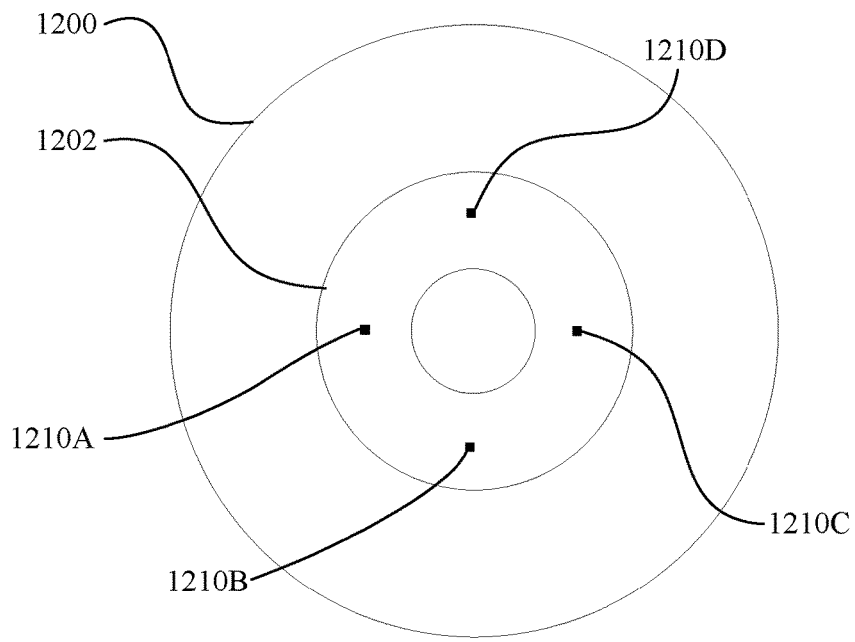
FIG. 12 illustrates a diagrammatic representation of evenly spaced ultrasound modules/transducers in accordance with at least one embodiment of the present invention.

In at least one embodiment as illustrated in FIG. 12 (omits the other components to facilitate presentation clarity), there are a plurality of ultrasound modules 1210A-1210D spaced around the contact lens 1202 on the eye 1200 to increase the fidelity of the communication link between the contact lenses through the nose. Although four ultrasound modules 1210A-1210D are illustrated, it should be appreciated based on this disclosure that a variety of numbers of ultrasound modules may be used with example numbers of ultrasound modules being any number between 2-8, a plurality of ultrasound modules, and at least one ultrasound module. The illustrated ultrasound modules 1201A-1210D are evenly spaced around the periphery of the contact lens 1202 where evenly spaced includes equal distance between the ultrasound modules (i.e., the same distance between neighboring ultrasound modules) and/or balanced about a diameter drawn through the contact lens 1202. In a further embodiment, the illustrated ultrasound modules are replaced by transducers that are multiplexed together as illustrated in FIG. 13 as described in detail subsequently.

In at least one embodiment, the system controller deactivates the transmission components of the ultrasound module when the respective contact lens is not transmitting. In a further embodiment, the illustrated ultrasound modules are replaced by transducers that are multiplexed together as illustrated in FIG. 13. In a further embodiment for contact lenses that have a plurality of ultrasound modules or at least a plurality of transmit/receive/transceiver transducers, the method includes having the system controller determine which ultrasound module/transducer provides the best response. The system controller selects the ultrasound module/transducer that produces a highest output response to received sound pressure waves. The system controller will deactivate the ultrasound module(s)/transducer(s) that were not selected (i.e., provided a lower signal strength). One benefit to this method is that as the contact lens rotates on the eye, the system controller can change the used ultrasound module/transducer to avoid any ultrasound module/transducer covered by an eyelid.

Figure 13:
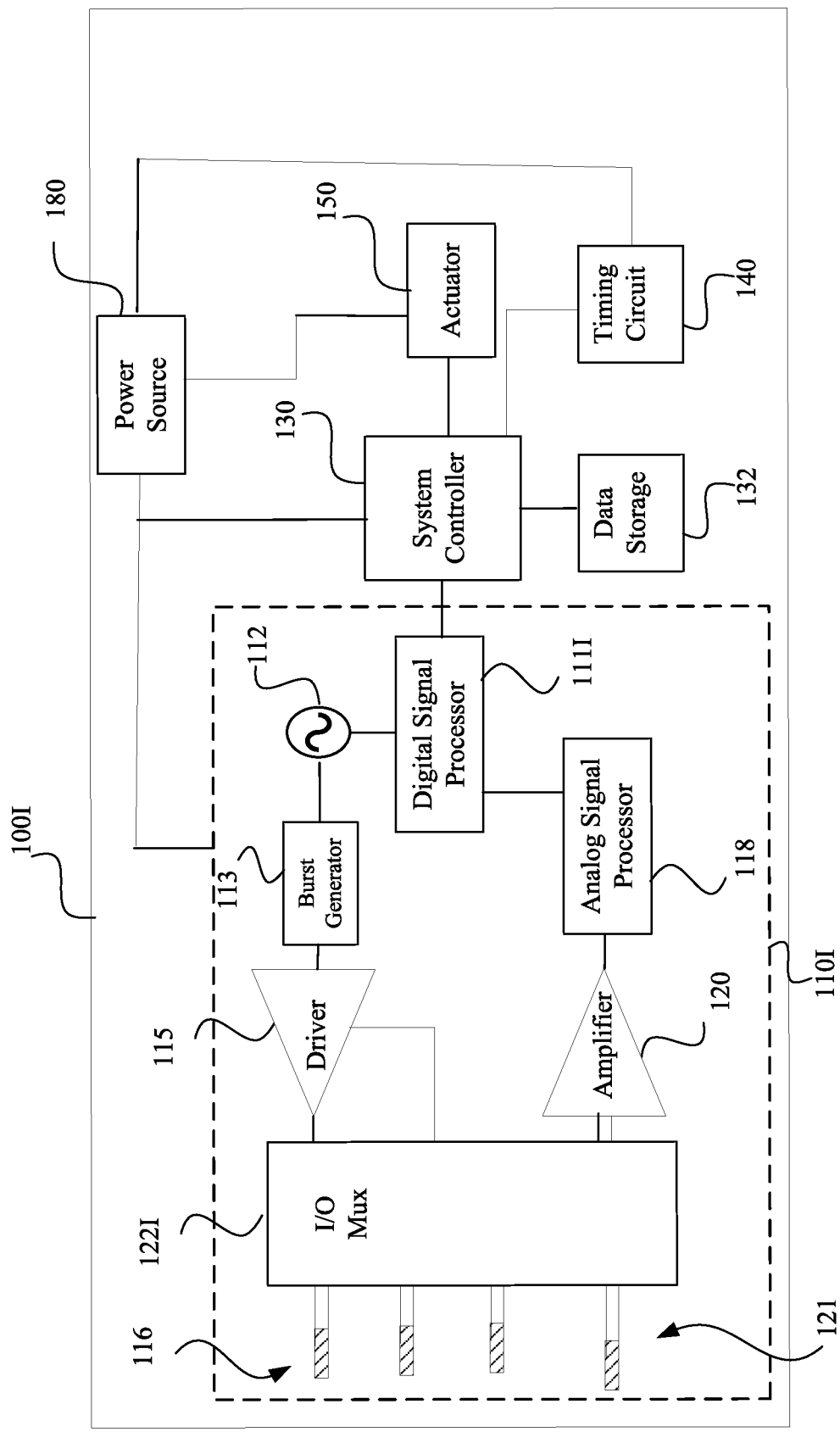
FIG. 13 illustrates an ultrasound module with a plurality of transmit/receive transducer pairs or transceiver transducers in accordance with at least one embodiment of the present invention.

In an alternative embodiment illustrated in FIG. 13, the contact lens 100I has one ultrasound module 110I having a plurality of transducers 116, 121 and an I/O multiplexer (mux) 122I attaching the transducers 116, 121 to the ultrasound module components discussed in the above embodiments. FIG. 13 illustrates the inclusion of the digital signal processor 111I, the oscillator 112, the burst generator 113, the driver 115, the amplifier 120, and the analog signal processor 118. In alternative embodiment, these ultrasound module components may be replaced by components from the other described ultrasound module embodiments including using just the transmit or receive paths of those embodiments. An advantage of this configuration is that it reduces the power requirements and weight considerations by eliminating duplicative components and allowing the ultrasound module to drive multiple transmit transducers and to receive analog signals from multiple receive transducers. In at least one embodiment, the transmit transducers and the receive transducers are distributed about the contact lens as discussed above in connection with FIG. 12. In a further embodiment, the transmit transducers and the receive transducers are grouped together in one area of the contact lens.

In at least one embodiment where the contact lens includes rotational stability features, then the number of ultrasound modules is one. The angle at which the transducer is relative to the electronics ring may be more severe such that a perpendicular line drawn from the transducer would intersect with the bridge (or just below the bridge) of most wearers of the intended population for the contact lens.

FIG. 14 is a flow chart that illustrates a method that may be used with more than one of the above-described system embodiments. The illustrated method provides an example of how communication may be facilitated between a contact lens and an external device, where the contact lens and the external device transmit communications embodying one or more messages intended for the other. In an alternative embodiment, the external device communicates with both contact lenses, for example providing processing power to process data generated by sensors on the contact lenses. In at least one embodiment, similar methods may be used for implanted intraocular lenses during use.

The contact lens receives a sound pressure wave that embodies a message from the external device, 1410. The contact lens uses a transducer in at least one ultrasound module, which in at least one embodiment is a dedicated receive transducer. When the contact lens has a common transceiver transducer to transmit and receive, then in at least one embodiment the transceiver transducer is in a default position of receive mode. The message may include data interpretation or instructions to perform a function such as with the actuator and/or a predefined function. In at least one embodiment, the message is created by the external device using a predetermined protocol for communication with the contact lens. The ultrasound module converts an analog signal representing the sound pressure wave received by the transducer to an electrical signal, 1420. The resulting output is provided by the ultrasound module to a system controller, 1430. The system controller decodes the electrical signal to learn the message from the processor of the external device, 1440.

The system controller sends a control signal that embodies a transmission message intended for the external device, 1450. The message may include sensor data, a request for sensor data, a request for confirmation of data interpretation (e.g., direction of focus and/or contact lens orientation), data interpretation, etc. In an alternative embodiment, the output signal preparation is omitted if the control signal is sufficient for driving the transducer, which may be a dedicated transmit transducer. The ultrasound module drives the transducer to produce at least one sound pressure wave based on the output signal, 1460. At 1470, the output signal is utilized to produce at least one sound pressure wave.

In an alternative embodiment, the external device is replaced by the other contact lens in these illustrated methods. In a further alternative embodiment, there are both the external device and other contact lens in communication with the contact lens.

FIG. 15 illustrates a method for the external device to generate a message to the contact lens in response to a message from the contact lens. The microphone on the external device receives a sound pressure wave from the contact lens embodying a message, 1510. The microphone of the external device provides an output to a processor on the external device, 1520. The processor on the external device converts the received output to the message from the contact lens 1530. The message may include sensor data, a request for sensor data, a request for confirmation of data interpretation (e.g., direction of focus and/or contact lens orientation), data interpretation, etc. The processor on the external device transmits a control signal for the speaker of the external device to propagate a sound pressure wave embodying a message intended for the contact lens, 1540. The control signal drives the speaker on the external device to propagate the sound pressure wave(s) embodying the message from the processor of the external device, 1550.

The contact lens receives the sound pressure wave from the external device, 1560. The contact lens uses its transducer, which in at least one embodiment is a dedicated receive transducer. When the contact lens has a common transceiver transducer to transmit and receive, then in at least one embodiment the transceiver transducer is in a default position of receive mode. The ultrasound module converts an analog signal representing the received sound pressure wave received by the transducer, 1570. The resulting output is provided by the ultrasound module to a system controller. The system controller converts the output into the message from the processor on the external device. In a further embodiment, the first contact lens performs a function based on the received message such as change the activation level of the lens.

In at least one embodiment, the steps illustrated in FIGS. 14 and 15 are rearranged, in part, based on groupings of steps performed by one contact lens or the external device. For example, steps 1410-1440 are steps performed by the contact lens in connection to message receipt, A; steps 1450-1470 are steps performed by the contact lens to generate a message, B; steps 1510-1540 are steps performed by the external device in connection to message receipt, C; and steps 1550-1570 are steps performed by the external device to generate a message, D.

In a further embodiment to the methods illustrated in FIGS. 14 and 15, the system controller deactivates the transmission components of the ultrasound module when the contact lens is not transmitting.

In a further embodiment, the message sent is a wake-up message (or start message) to activate the ultrasound module(s) on the contact lens. In at least one implementation, the contact lens will activate for short periods of time at a predetermined sampling rate to detect the wake-up message being broadcasted by the external devices or the other contact lens at a predetermined broadcast rate. In at least one embodiment the predetermined sampling rate and the predetermined broadcast rate are at different frequencies where one rate is faster than the other to allow for the sampling and the broadcasting to intersect eventually. Alternatively, the short period of time is of sufficient length to cover the frequency period for the predetermined broadcast rate or slightly longer to address a situation where the clock frequencies of the contact lens and the message source may be different. A wake-up message may be used for initial activation of the contact lens along with reactivation of the contact lens, for example, when the contact lenses are in a slower operational or sleep state when the wearer is asleep or resting or alternatively has set the operational mode to a state in which communication between the contact lenses is not necessary. In a further embodiment, the wake-up message is sufficient strength and length to facilitate the contact lens generating sufficient power to activate in response to the wake-up message such as the energy harvester being activated by the current generated by the receive transducer.

In a further embodiment, the sound pressure waves produced by the contact lens and external device, respectively, are at different frequencies such as the contact lens using a first frequency and the external device using a second frequency. The ultrasound module in at least one embodiment then is tuned for the frequency of the output sound pressure wave produced by the external device. An advantage of this is that it improves both the contact lens' and the external device's receiver's capability of correctly detecting the desired signal. By using separate frequencies, frequency selective techniques (such as mixing and envelope detection) can reject noise or undesired transmit signals that could interfere with communication.

In a still further embodiment, the oscillation frequency of the ultrasound module is calibrated to propagate sound pressure waves at multiple frequencies. For example, in at least one embodiment, the first contact lens, the second contact lens, and the external device use three different frequencies between them to facilitate tracking the source of each message. To this end a third receive path may be added to the above embodiments to enable the ultrasound module to propagate sound pressure waves at three discrete frequencies. Alternatively, the ultrasound module may have two receive paths having transducers configured to receive sound pressure waves at the frequency used by the external device and the frequency used by the other contact lens.

The oscillation frequency in each ultrasound module may be calibrated in a number of ways. The timing circuit may be configured to analyze any received message to determine its frequency, or to transmit a timing signal based on timing setpoint values. Moreover, in embodiments, additional programmable circuitry for frequency calibration may be included in ultrasound module subject to power and cost constraints. In at least one alternative embodiment, the first lens and the second lens are calibrated after manufacture to function as a left lens and a right lens. In at least one of these alternative embodiments calibration is achieved by establishing communication with the external device and transmitting calibration instructions, including for example frequencies to be used by the ultrasound module, using the external device. In an alternative embodiment, an external FOB is used to set the contact lenses' frequencies, for example using ultrasound, radio frequency or light.

In a further embodiment for contact lenses that have a plurality of ultrasound modules or at least transmit/receive/transceiver transducers, the method includes having the system controller determine which ultrasound module/transducer provides the best communication path. The system controller selects the ultrasound module/transducer that produces a highest output response to the sound pressure wave produced by the external device. This measurement may be made during performance of the above-described communication methods or a communication consisting of pinging back and forth between the contact lens and the external device. The pinging communication may occur on a predetermined schedule or at predetermined intervals possibly even as part of a clock synchronization between the contact lens and the external device. The system controller will deactivate the ultrasound module(s)/transducer(s) that were not selected (i.e., provided a lower signal strength). One benefit to this method is that as the contact lens rotates on the eye, the system controller can change the used ultrasound module/transducer for communication with the external device.

One approach to facilitate the communication between the contact lens and the external device is to implement automatic frequency control for the communication channel. In at least one embodiment, the external device would be the master and communicate configuration instructions upon establishing communication protocol with the at least one contact lens. Automatic frequency control may be used to enhance the connection between the external device and the at least one contact lens. In an alternative embodiment the timing circuit on the contact lens would be the master. The clock synchronization in at least one embodiment will lead the electronics to be biased towards a lens pair to have one be a master. In a further embodiment, the selection of the master contact lens is made post-manufacturing via a software download to the lenses and/or settings change. This approach also could be used to facilitate the dual frequency approach discussed in this disclosure.

In at least one embodiment the external device initiates the configuration sequence for establishing a communication protocol with the contact lens(es). The external device transmits a start signal to the contact lens(es). In at least one embodiment, the contact lens(es) is in low power consumption mode having its transmission components deactivated and only receive components active to conserve power. This operation state may be programmed into the system controller initialization protocol. The received start signal from the external device causes each contact lens(es) to generate a random string. In embodiments the string is an 8-bit random number. The string may be used to set an 8-bit current steered digital to analog converter, which in turn sets bias current for the oscillator, i.e. the frequency, of each lens. The timing circuit clock function is tuned to the oscillator frequency. Each lens encodes the string and propagates a sound pressure wave corresponding to the string. The external device decodes the received sound pressure wave. Once the external device determines the strings from each lens are different, e.g. each lens is using a different frequency, the external device establishes communication protocol with each lens. An advantage of this embodiment is encoding two generic lenses for operation as a left lens and a right lens. The external device may be configured with specific software consistent with this method. It is understood by one of ordinary skill in the art that a suitable external device has capability to propagate sound pressure waves across the frequency band used by the ultrasound module of each contact lens.

In at least one further embodiment to the above method embodiments, similar methods can be used for implanted intraocular lenses during use.

Although shown and described in what is believed to be the most practical embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic lens system configured for ultrasound communication with an external device comprising:
   at least one ophthalmic lens;
   at least one ultrasound module in said ophthalmic lens, at least one of said at least one ultrasound module includes at least one transducer front-facing and orientated such that when a sound pressure wave is produced, the sound pressure wave travels outwardly from said ophthalmic lens,
   a system controller in electrical communication with said at least one ultrasound module, said system controller configured to provide a control signal to said at least one ultrasound module where the control signal includes a message to be transmitted by said at least one ultrasound module, said system controller configured to receive an output from said at least one ultrasound module and to perform a function in response to a receive message embodied in the output, and
   a timing circuit in electrical communication with said system controller, said timing circuit configured to produce a timing signal when said system controller is activated.

2. The ophthalmic lens systems according to claim 1, wherein said ophthalmic lens is a contact lens.

3. The ophthalmic lens systems according to claim 1, wherein said ophthalmic lens is an intraocular lens.

4. The ophthalmic lens system according to claim 1, wherein said at least one ultrasound module includes a plurality of ultrasound modules evenly distributed around a perimeter of said ophthalmic lens.

5. The ophthalmic lens system according to claim 4, wherein said system controller is configured to activate said ultrasound module that produces the strongest output in response to a received sound pressure wave, and
said system controller configured to deactivate said at least one other ultrasound module on said ophthalmic lens.

6. The ophthalmic lens system according to claim 1, wherein
said at least one transducer includes a transmit transducer and a receive transducer, and
each ultrasound module includes
a processor in electrical communication with said system controller;
a transmit path having
an oscillator in electrical communication with said processor,
a burst generator in electrical communication with said oscillator and said processor,
a transmit driver in electrical communication with said burst generator configured to receive a burst signal from said burst generator,
said transmit transducer in electrical communication with said transmit driver; and
at least one receive path having
said receive transducer,
a receive amplifier in electrical communication with said receive transducer and configured to amplify an output of said receive transducer, and
an analog signal processor in communication with said receive amplifier and said processor, and
wherein said processor configured to control whether said transmit path and said at least one receive path are activated.

7. The ophthalmic lens system according to claim 6, wherein each ultrasound module includes two receive paths,
said two receive paths each having said receive transducer tuned to different frequencies from the other receive paths.

8. The ophthalmic lens system according to claim 1, wherein said at least one ultrasound module includes three receive paths,
said three receive paths each having said receive transducer tuned to different frequencies from the other receive paths.

9. The ophthalmic lens system according to claim 1, wherein
said at least one transducer is one transducer, and
each ultrasound module includes
a processor in electrical communication with said system controller;
said transducer;
a switch in electrical communication with said processor;
a transmit path having
an oscillator in electrical communication with said processor,
a burst generator in electrical communication with said oscillator and said processor,
a transmit driver in electrical communication with said burst generator configured to receive a burst signal from said burst generator, said transmit driver drives said transducer when connected through said switch; and
at least one receive path having
a receive amplifier in electrical communication with said transducer through said switch and configured to amplify an output of said transducer, and
an analog signal processor in communication with said receive amplifier and said processor, and
wherein said processor configured to control whether said transmit path and said at least one receive path are activated based on an operation mode of said ultrasound module between transmit and receive, and
said processor configured to control said switch and the operation mode.

10. The ophthalmic lens system according to claim 1, wherein
each ophthalmic lens includes a power source in electrical communication with said system controller and said at least one ultrasound module;
said at least one transducer includes a transmit transducer and a receive transducer; and
each ultrasound module includes
a processor in electrical communication with said system controller;
a transmit path having
an oscillator in electrical communication with said processor,
a pulse generator in electrical communication with said oscillator and said processor,
a charge pump in electrical communication with said power source,
a transmit driver in electrical communication with said pulse generator and said charge pump, said transmit driver configured to receive a signal from said pulse generator,
said transmit transducer in electrical communication with said transmit driver; and
at least one receive path having
said receive transducer,
a receive amplifier in electrical communication with said receive transducer and configured to amplify an output of said receive transducer, and
an envelope detector in electrical communication with said receive amplifier,
an analog signal processor in communication with said envelope detector and said processor, and
wherein said processor configured to control whether said transmit path and said at least one receive path are activated.

11. The ophthalmic lens system according to claim 1, wherein
each ophthalmic lens includes a power source in electrical communication with said system controller and said at least one ultrasound module;
said at least one transducer includes a transmit transducer and a receive transducer, and
each ultrasound module includes
a processor in electrical communication with said system controller;
a transmit path having
an oscillator in electrical communication with said processor,
an amplitude modulation modulator in electrical communication with said oscillator and said processor,
a charge pump in electrical communication with said power source,
a transmit driver in electrical communication with said amplitude modulation modulator and said charge pump, said transmit driver configured to receive a signal from said amplitude modulation modulator, said transmit transducer in electrical communication with said transmit driver; and
at least one receive path having
said receive transducer,
a receive amplifier in electrical communication with said receive transducer and configured to amplify an output of said receive transducer, and
an envelope detector in electrical communication with said receive amplifier,
an analog signal processor in communication with said envelope detector and said processor, and
wherein said processor configured to control whether said transmit path and said at least one receive path are activated.

12. The ophthalmic lens system according to claim 1, wherein at least one ultrasound module includes at least one transducer angled relative to an imaginary plane taken at a bottom edge of the said ophthalmic lens on which said at least one transducer is located.

13. The ophthalmic lens system according to claim 1, further comprising a data storage unit in electrical communication with said system controller.

14. The ophthalmic lens system according to claim 13, wherein said data storage unit includes at least one memory data register.

15. The ophthalmic lens system of claim 1, wherein said transducer in said at least one ultrasound module is configured to receive the sound pressure wave at a frequency of approximately 20 kHz.

16. A method for facilitating communication between an ophthalmic lens when being used by a person where said ophthalmic lens includes at least one ultrasound module in electrical communication with a system controller, the ultrasound module having a forward facing transmit transducer, and an external device having at least a processor, a speaker and a microphone, said method comprising:
receiving a sound pressure wave propagated by an external device at the ultrasound module;
converting with the ultrasound module the sound pressure wave to an electrical signal;
providing an output to the system controller from the ultrasound module;
converting with the system controller the output into the message from the processor on the external device;
sending a control signal from the system controller to the ultrasound module where the control signal embodies a transmission message intended for the external device;
preparing an output signal for the transmit message by the ultrasound module; and
driving the ultrasound module based on the output signal to produce at least one sound pressure wave.

17. The method according to claim 16, further comprising:
receiving a sound pressure wave from an ophthalmic lens at the microphone on the external device;
converting the received sound pressure wave to an electrical signal;
providing an output to a processor;
converting with the processor the received output to the message from the ophthalmic lens;
sending a control signal with the processor embodying a message intended for the ophthalmic lens;
driving the speaker based on the control signal to produce at least one sound pressure wave;
receiving a sound pressure wave propagated by an external device at the ultrasound module;
converting with the ultrasound module the sound pressure wave to an electrical signal;
providing an output to the system controller from the ultrasound module; and
converting with the system controller the output into the message from the processor on the external device.

18. The method according to claim 17, wherein the sound pressure waves produced by the ophthalmic lens and external device are at different frequencies.

19. The method according to claim 18, wherein the transducer in the at least one ultrasound module is tuned to the frequency of the output transducer of the external device and a second receive transducer in the at least one ultrasound module is tuned to the frequency of the ophthalmic lens.

20. The method according to claim 16, wherein the ophthalmic lens includes a plurality of ultrasound modules evenly distributed around the periphery of the ophthalmic lens; and
the method further comprising:
selecting by the at least one system controller the ultrasound module that produces a strongest output in response to the received sound pressure wave propagated by the external device, and
deactivating by the at least one system controller the non-selected ultrasound modules.

21. The method according to claim 16, further comprising deactivating the transmission components of the ultrasound module when not transmitting.

22. The method according to claim 16, wherein the message sent by the system controller of the ophthalmic lens uses a predefined protocol.

23. The method according to claim 16, wherein the message sent by the system controller of the ophthalmic lens includes at least one of instructions for the external device to perform a predefined function and sensor readings from at least one sensor on the ophthalmic lens.

24. The method according to claim 16, further comprising:
transmitting a start signal from the external device to each ophthalmic lens;
receiving the start signal and tuning the frequency of the transmit transducer to a randomly selected frequency by the ultrasound module;
propagating a sound pressure wave encoding a message identifying the selected frequency by the ultrasound module of each ophthalmic lens; and
decoding the messages from each ophthalmic lens and establishing communication protocol with each ophthalmic lens when the messages do not identify the same frequency.

* * * * *